United States Patent [19]

Larsson et al.

[11] Patent Number: 6,020,453
[45] Date of Patent: Feb. 1, 2000

[54] LACTIC ACID EXCRETING POLYLACTIDE SHEET FOR USE IN ABSORBENT ARTICLES

[75] Inventors: Björn Larsson, Billdal; Erik Lagerström, Mönlycke, both of Sweden

[73] Assignee: SCA Molnlycke Products AB, Goteborg, Sweden

[21] Appl. No.: 08/849,768

[22] PCT Filed: Dec. 5, 1995

[86] PCT No.: PCT/SE95/01455

§ 371 Date: Jun. 12, 1997

§ 102(e) Date: Jun. 12, 1997

[87] PCT Pub. No.: WO96/18422

PCT Pub. Date: Jun. 20, 1996

[30] Foreign Application Priority Data

Dec. 13, 1994 [SE] Sweden .................................. 9404348

[51] Int. Cl.⁷ ............................ C08G 63/00; A61L 15/46
[52] U.S. Cl. ....................... 528/272; 528/302; 528/308.2; 528/308.3; 528/354; 528/355; 428/480
[58] Field of Search ................................ 528/308.3, 272, 528/302, 308.2, 354, 355; 428/480

[56] References Cited

U.S. PATENT DOCUMENTS

| | | | |
|---|---|---|---|
| 3,794,034 | 2/1974 | Jones, Sr. ................................. | 128/290 |
| 5,444,113 | 8/1995 | Sinclair et al. ........................... | 524/306 |
| 5,760,118 | 6/1998 | Sinclair et al. ........................... | 524/306 |
| 5,763,098 | 6/1998 | Kameoka et al. ....................... | 428/481 |

FOREIGN PATENT DOCUMENTS

| | | |
|---|---|---|
| 0 130 356 | 1/1985 | European Pat. Off. . |
| 2 309 575 | 9/1974 | Germany . |
| 4-168149 | 6/1992 | Japan . |
| 6-149169 | 5/1994 | Japan . |
| 8505491 | 11/1985 | Sweden . |
| 9100364 | 4/1991 | Sweden . |
| 2 107 192 | 4/1983 | United Kingdom . |
| 2 277 324 | 10/1994 | United Kingdom . |
| WO 94/07941 | of 0000 | WIPO . |
| WO 90/01521 | 2/1990 | WIPO . |
| WO 91/08726 | 6/1991 | WIPO . |
| WO 92/04412 | 3/1992 | WIPO . |
| WO 92/04413 | 3/1992 | WIPO . |

*Primary Examiner*—P. Hampton-Hightower
*Attorney, Agent, or Firm*—Young & Thompson

[57] ABSTRACT

Surface material for an absorbent article, wherein the material includes a surface layer which excretes lactic acid and/or an acid physiologically acceptable derivative thereof when the surface layer is immersed in a water volume, the weight ratio between surface layer and water volume being 1:100, in an amount such that the lactic acid and/or derivative excreted within a time period of at most 20 hours will impart a pH of at most 3.0 to the water volume.

11 Claims, No Drawings

LACTIC ACID EXCRETING POLYLACTIDE SHEET FOR USE IN ABSORBENT ARTICLES

FIELD OF THE INVENTION

The present invention relates to surface material for absorbent articles in the form of tampons, sanitary napkins, diapers or incontinence guards, for instance, preferably tampons and sanitary napkins.

BACKGROUND OF THE INVENTION

It is known that a rich flora of primarily lactic acid-producing bacteria occur in the urogenital region of healthy women, both before and after the menopause. These bacteria have antagonistic properties against different occurring uropathogens, which is thought to be due to their ability to produce different antimetabolites. A particularly important antimetabolite is, of course, lactic acid which has an inhibiting effect on different pathogenic microorganisms by lowering the pH in the urogenital environment.

It is also known that the production of lactic acid is disturbed in conjunction with menstruation, resulting in a decrease in the amount of lactic acid produced. This will, of course, result in a higher pH-value, which favours those microorganisms that generate bad-smelling substances, among other things. The growth of microorganisms is also liable to cause irritation of the skin and the mucous membrane in the urogenital region.

Those methods afforded by known techniques in counteracting these problems to a large extent involve the use of different tampons and sanitary napkins which have been impregnated with different substances that lower the pH-value in the present context. For instance, SE 9100364-0 and SE 8505491-4 describe tampons and napkins which have been impregnated with cultures of living lactic acid bacteria. Even though this type of technical solution would seem to be sympathetic at first sight, since there are used lactic acid bacteria which occur naturally in the urogenital region, a closer study of these specifications reveals that the technique applied is both very complicated and highly sensitive. For instance, it is necessary to isolate the bacteria cultures and to determine their type before they can be finally incorporated in the tampon or the napkin with the aid of some form of adhesive. A further drawback with this technique, as pointed out in EP-Al 0,130,356, is that the pH-value in the vagina in conjuction with menstruation already lies in the alkaline region when the tampon or the napkin is applied. This inhibits the growth of the lactic acid bacteria and therewith reduce their lactic acid production, or at least cause this production to fluctuate greatly.

The last-mentioned document, EP-Al 0,130,356, describes in turn a tampon whose absorbent body is impregnated with a citrate-containing buffer solution. Naturally, a buffer solution of this nature must be considered foreign to the body at least in the present context, although the most serious drawback with this technical solution resides, also in this case, in the additional and complicated working steps occasioned by the actual impregnation process in tampon manufacture.

Other technical solutions are described in U.S. Pat. No. 3,794,034 and DE-Al 2,309,575. These solutions, however, are also encumbered with the same drawbacks.

A somewhat different technical solution is described in GB-A-2,107,192, which relates to a tampon which may have a polylactic acid for instance incorporated in its absorbent body. It is proposed that this polymer is admixed in the fibre pulp of the absorbent body, in a powder, granule or fibre form. This technical solution thus also necessitates the application of at least one additional stage in the manufacture of the tampon, namely the stage in which the polylactic acid is mixed in the fibre pulp. The object of the tampon is to lower the pH-value within the tampon, whereas, on the other hand, the pH-value externally of the tampon is permitted to adopt such high values as 4.5.

WO 91/08726 also describes the use of polylactic acid in absorbent articles, more specifically in the top and bottom sheets of such articles. These sheets, however, are designed solely to fulfil a specific purpose, namely that the absorbent article shall be considered to represent an article which is biologically degradable after use. The document makes no mention of the possibility that the polylactic acid could be used to adjust the pH-value with the purpose of counteracting bad smells or irritation of the skin/mucous membrane.

JP 61-149 160 also describes the use of polylactic acid in absorbent articles for medical purposes. In this case, the polylactic acid is present in the form of a sponge. The only reason given for the use of precisely polylactic acid is to render the sponge biologically degradable.

WO 90/01521 describes plastic films comprised of polylactic acid, among other things. However, these plastic films are intended solely for conventional packaging purposes. The document gives no indication that the film could be used in absorbent articles.

There is an obvious need for biologically degradable tampons and sanitary napkins with which bad smells and the risk of irritation of the skin and mucous membrane in the urogenital region of the user can be counteracted and controlled continuously when the article is in use, and which can also be produced in a simple fashion.

SUMMARY OF THE INVENTION

The object of the present invention is to provide an absorbent article which satisfies this need.

This object is achieved in accordance with the present invention with the aid of a surface material of the kind mentioned in the introduction that has the characteristic features set forth in the independent claim which is able to ensure that the concentration of lactic acid and/or lactic acid derivative in the urogenital region of menstruating women using an absorbent article provided with such surface material will be sufficient in use, and will remain sufficient in use, to establish a pH-value of at most 4.0 in this region.

Different embodiments of the present invention will be apparent from the following dependant claims.

The outer layer of the surface material will preferably be comprised essentially of at least a lactic acid-based polyester, or as this polymer is also called, a polylactide i.e. a polymer of the formula

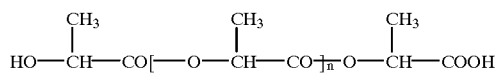

where n is the number of monomer units in the average polymer chain. The number-average molecular mass, $M_n$, is preferably at most 50,000, and more preferably at most 40,000.

It should be noted that the expression "lactic acid-based polyester" as used here will also include polymers of the aforesaid formula in which one or more hydrogen atoms are replaced with one or more suitable groups, for instance methyl or ethyl.

The aforesaid surface layer may be the outermost layer of the surface material, although it may also form a major part of the surface material or the whole of said material. The surface material may be comprised of an outer layer of the aforesaid kind that is deposited on a substrate consisting of high molecular weight polylactide, i.e. a polylactide for which $M_n$>50,000, although the substrate may also be comprised of some other suitable material, for instance a polymer, such as polyethylene, polypropylene, a polyester or the like; it is also conceivable for the substrate to include or to consist of mixtures of such polymers. The surface material, or in certain cases at least the substrate, will conveniently have those properties that are normally required of a surface material with regard to its liquid permeability, softness, mechanical strength, stretchability, and so on. The substrate may be imparted these properties, by introducing different additives, such as a softener, for instance.

According to one preferred embodiment, the lactic acid-based polyester is modified to include relatively large areas of amorphous material as it has been found that amorphous material will hydrolyze more rapidly than crystalline material, probably because of its higher permeability to water and vapour respectively, which means that the amorphous material will be converted more rapidly to lactic acid and/or lactic acid derivative. Examples of known methods of adjusting the crystallinity of lactic acid-based polyester, for instance so as to obtain a practically amorphous polyester, are described in WO 94/07941 (see Example 26 in said document, for instance).

The lactic acid-based polyester will naturally contain a given quantity of monomers and/or oligomers necessitated by the laws of nature, for instance lactide when the polyester is polylactide; the equilibrium concentration with regard to lactide is normally about 1–3 percent by weight, calculated on the polylactide. Since there is reason to assume that the monomer will decompose quickly to lactic acid and/or lactic acid derivative than the corresponding polyester, the polyester layer is preferably modified to have a higher monomer and/or oligomer concentration than the equilibrium concentration. This higher concentration is preferably 10%-units, more preferably 5%-units greater than the corresponding equilibrium concentration. When the polyester is polylactide, the monomer/-oligomer concentration, i.e. the lactide concentration, will preferably be 5–30 percent by weight, more preferably 10–25 percent by weight, calculated on the polylactide. By "oligomer" is meant in this document a polymer which comprises at most 10 mers. Known methods of achieving the aforesaid increases in concentration are described, for instance, in WO 90/01521, see for instance page 11, lines 24–32, or page 18, lines 19–34.

In another preferred embodiment, the outer sheet or surface layer includes an agent which accelerates depolymerization of the polyester and/or conversion of the polyester and/or its monomer/oligomers to lactic acid and/or lactic acid derivative, at least when the absorbent article is worn. Examples of such agents are mentioned in JP-A 4,168,149 and include such enzymes as lipase, amylase cellulase and enzymes for dehydrogenating lactic acid.

By treating the polyester in the surface layer with water and/or water vapour, the polyester can be prehydrolyzed so that the polyester will be converted to lactic acid and/or lactic acid derivative to a greater extent than would otherwise be the case, at least when the article is in use.

DETAILED DESCRIPTION OF THE INVENTION

Further embodiments of the present invention will be apparent from the claims dependent on claim 1.

In addition to the aforementioned methods of modifying a lactic acid-based polyester with the intention of producing more lactic acid in the use in question, there are a number of other methods known to the person skilled in this art for achieving such modification, as will be evident from page 9, lines 17–25 of WO 92/04412.

The present invention is described below in more detail with reference to an Example.

EXAMPLE

Different surface layer materials which included polylactide were immersed in water at room temperature. The pH of the water was measured immediately after immersing the material and also after the material had remained immersed for about 20 hours. About 0.4 g material was immersed in about 40 ml of water in each test. It was then possible to calculate the amount of lactic acid released on the basis of these data.

There was used as reference material a polylactide film which consisted to about 95% of polymerized L-lactic acid; this film is referred to below as Film 1. In addition to this film, there were also used a carded, thermobonded nonwoven material, a spun-bonded nonwoven material, staple fibres, and a carded, thermobonded nonwoven material made from these staple fibres; all these polylactide materials were essentially of the same non-modified type as Film 1.

The surface layer was used as surface material according to the present invention in three tests. These surface layers comprised polylactide films which had been modified to include an elevated monomer/oligomer concentration. One film had a monomer/oligomer concentration of about 24 percent by weight and is referred to below as Film 2. The corresponding concentration in another film, referenced Film 3, was about 11 percent by weight. A third film had a concentration of about 14 percent by weight.

The following Table sets forth the pH-values and the calculated amount of lactic acid released in percent by weight based on the original weight of the material concerned in the tests carried out on the aforesaid materials.

| Non-modified material | $M_n M_w \times$ 1000 | pH immediately after immersion | Released lactic acid in percent by weight immediately after immersion | pH after 20 hours immersion | Released lactic acid in percent by weight after 20 hours immersion |
|---|---|---|---|---|---|
| Film 1 | 60/135 | 5.9 | 0 | 3.2 | 0.6 |
| Carded and thermobonded nonwoven | 62/137 | 4.5 | 0.03 | 3.5 | 0.3 |
| Spunbonded | 85/180 | 5.8 | 0 | 4.3 | 0.05 |

-continued

| Non-modified material | $M_n M_w \times 1000$ | pH immediately after immersion | Released lactic acid in percent by weight immediately after immersion | pH after 20 hours immersion | Released lactic acid in percent by weight after 20 hours immersion |
|---|---|---|---|---|---|
| nonwoven Staple fibres | 65/140 | 4.5 | 0.03 | 3.4 | 0.3 |
| Carded and thermobonded nonwoven made from staple fibres | 58/139 | 4.3 | 0.05 | 3.1 | 0.6 |
| Modified material monomer in percent by weight within parenthes is | | | | | |
| Film 2 (24%) | 37/92 | 2.8 | 1.3 | 2.6 | 2.5 |
| Film 3 (11%) | 35/107 | 4.0 | 0.1 | 3.0 | 0.9 |
| Film 4 (14%) | 33/94 | 3.7 | 0.2 | 2.9 | 1.2 |

$M_n$ = the number-average molecular mass
$M_w$ = the weight-average molecular mass It will be seen from the Table that the non-modified materials gave the water volume in question a pH-value of at the lowest 3.1 after 20 hours treatment, whereas all the modified materials gave a pH-value of 3.0 or lower over a corresponding time period. The difference in released lactic acid is still more dramatic: In the case of the non-modified materials, the highest value was 0.6%, whereas the lowest value for the modified materials was 0.9%. It will also be seen from the Table that the pH-values obtained immediately with the non-modified materials were not lower than 4.3 (corresponding to 0.05% released lactic acid), while the highest pH-value of the modified materials did not exceed 4.0 (corresponding to 0.1% released lactic acid).

Naturally, the present invention shall not be considered to be restricted to the aforedescribed exemplifying embodiments thereof or to the Example, and it will be understood that the invention is solely restricted by the following claims, within whose scope other embodiments will be conceivable to the person skilled in this art. For instance, the inventive surface material may be used to counteract bad smells generated in the use of diapers or incontinence guards.

We claim:

1. Surface material for an absorbent article, including a surface layer mainly consisting of at least one lactic acid-based polyester which excretes lactic acid and/or an acid physiologically acceptable derivative thereof when the surface layer is immersed in a volume of water, wherein the weight ratio between the surface layer and the water volume is 1:100, in an amount such that lactic acid and/or derivative that is excreted within a time period of at most 20 hours will impart to the water volume a pH of at most 3.0, said surface layer having prior to immersion in the water volume, a monomer and/or oligomer concentration which is essentially greater than the equilibrium concentration of monomer and/or oligomer corresponding to the amount of polyester present, the monomer and/or oligomer concentration being 5–30 percent by weight calculated on the polyester.

2. Surface material according to claim 1, wherein the monomer and/or oligomer concentration is 10–25 percent by weight calculated on the polyester.

3. Surface material according to claim 1, wherein the lactic acid-based polyester, when the surface layer is immersed in said water volume, being partly converted in and/or outside the surface material to lactic acid and/or the acid, physiologically acceptable derivative thereof, said acid and/or said derivative then being excreted.

4. Surface material according to claim 3, wherein the polyester, when the surface layer is immersed in the water volume, being partly depolymerized to a monomer and/or oligomer which is or are then converted to lactic acid.

5. Surface material according to claim 3, wherein at least a part of the total amount of polyester has the formula

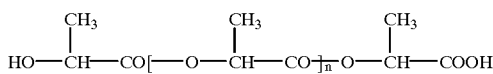

the number-average molecular mass, $M_n$, of this polyester being at most 50,000.

6. Surface material according to claim 5, wherein $M_n$ is at most 40,000.

7. Surface material according to claim 1, wherein the monomer and/or oligomer concentration exceeds the equilibrium concentration by up to 10%-points.

8. Surface material according to claim 7, wherein the monomer and/or oligomer concentration exceeds the equilibrium concentration by up to 5%-points.

9. Surface material according to claim 1, wherein the polyester is a polylactide and the monomer and/or the oligomer or the oligomers are lactides.

10. Surface material according to claim 1, wherein the surface layer includes an agent which accelerates the conversion of the polyester to lactic acid and/or lactic acid derivative, at least when the surface layer is immersed in said water volume.

11. Surface material according to claim 1, wherein the surface layer includes an agent which accelerates both the depolymerization of the polyester and conversion of the polyester and its monomer to lactic acid and/or lactic acid derivative, at least when the surface layer is immersed in said water volume.

* * * * *

UNITED STATES PATENT AND TRADEMARK OFFICE
CERTIFICATE OF CORRECTION

PATENT NO. : 6,020,453
DATED : February 1, 2000
INVENTOR(S) : Bjorn LARSSON et al.

It is certified that error appears in the above-indentified patent and that said Letters Patent is hereby corrected as shown below:

On the title page, amend Item [73] as follows:

--[73]    Assignee:    SCA Hygiene Products AB,

Goteborg, Sweden--.

Signed and Sealed this

Tenth Day of October, 2000

Attest:

Q. TODD DICKINSON

*Attesting Officer*    *Director of Patents and Trademarks*